US012702683B2

(12) United States Patent
Itescu

(10) Patent No.: US 12,702,683 B2
(45) Date of Patent: Aug. 11, 2026

(54) METHOD FOR IMPROVING VISUAL ACUITY

(71) Applicant: MESOBLAST INTERNATIONAL SÁRL, Meyrin (CH)

(72) Inventor: Silviu Itescu, Melbourne (AU)

(73) Assignee: Mesoblast International Sárl, Meyrin (CH)

( * ) Notice: Subject to any disclaimer, the term of this patent is extended or adjusted under 35 U.S.C. 154(b) by 868 days.

(21) Appl. No.: 17/420,325

(22) PCT Filed: Jan. 3, 2020

(86) PCT No.: PCT/IB2020/050032
§ 371 (c)(1),
(2) Date: Jul. 1, 2021

(87) PCT Pub. No.: WO2020/141483
PCT Pub. Date: Jul. 9, 2020

(65) Prior Publication Data

US 2022/0079991 A1 Mar. 17, 2022

Related U.S. Application Data

(60) Provisional application No. 62/788,037, filed on Jan. 3, 2019.

(51) Int. Cl.
*A61K 35/28* (2015.01)
*A61K 9/00* (2006.01)
*A61P 27/10* (2006.01)

(52) U.S. Cl.
CPC ............ *A61K 35/28* (2013.01); *A61K 9/0019* (2013.01); *A61K 9/0048* (2013.01); *A61P 27/10* (2018.01)

(58) Field of Classification Search
CPC .... A61K 35/28; A61K 9/0019; A61K 9/0048; A61P 27/10; A61P 27/02
See application file for complete search history.

(56) References Cited

U.S. PATENT DOCUMENTS 5,139,941 A 8/1992 Muzyczka et al.
5,173,414 A 12/1992 Lebkowski et al.
5,197,985 A 3/1993 Caplan et al.
5,226,914 A 7/1993 Caplan et al.
5,486,359 A 1/1996 Caplan et al.
5,591,625 A 1/1997 Gerson et al.
5,643,736 A 7/1997 Bruder et al.
5,736,396 A 4/1998 Bruder et al.
5,827,740 A 10/1998 Pittenger
5,855,619 A 1/1999 Caplan et al.
5,908,784 A 6/1999 Johnstone et al.
5,965,436 A 10/1999 Thiede et al.
6,022,540 A 2/2000 Bruder et al.
6,030,836 A 2/2000 Thiede et al.
6,149,906 A 11/2000 Mosca
6,261,549 B1 7/2001 Fernandez et al.
6,328,960 B1 12/2001 McIntosh et al.
6,355,239 B1 3/2002 Bruder et al.
6,387,367 B1 5/2002 Davis-Sproul et al.
6,482,231 B1 11/2002 Abatangelo et al.
6,541,024 B1 4/2003 Kadiyala et al.
6,685,936 B2 2/2004 McIntosh et al.
6,761,887 B1 7/2004 Kavalkovich et al.
6,797,269 B2 9/2004 Mosca et al.
6,835,377 B2 12/2004 Goldberg et al.
7,153,500 B2 12/2006 Qasba et al.
7,491,388 B1 2/2009 Mcintosh et al.
8,486,695 B2 7/2013 Danilkovitch et al.
8,592,209 B2 11/2013 Khurgel et al.
8,637,004 B2 1/2014 Danilkovitch et al.
9,050,178 B2 6/2015 Barry et al.
9,074,189 B2 * 7/2015 Mistry .................... A61P 27/12
9,301,978 B2 4/2016 Itescu et al.
9,598,673 B2 3/2017 Ichim
9,694,035 B2 7/2017 Aggarwal et al.
9,828,586 B2 11/2017 Tom et al.
9,943,547 B2 4/2018 Aggarwal et al.
9,963,678 B2 5/2018 Tom et al.
10,105,394 B2 10/2018 Itescu et al.
10,206,951 B2 2/2019 Bernard
10,400,218 B2 9/2019 Itescu et al.
(Continued)

FOREIGN PATENT DOCUMENTS

CN 108715833 A 10/2018
CN 112522191 A 3/2021
(Continued)

OTHER PUBLICATIONS

Bolontrade, M.F., et al., "A specific subpopulation of mesenchymal stromal cell carriers overrides melanoma resistance to an oncolytic adenovirus," Stem Cells Dev 21(14):2689-2702, Mary Ann Liebert, United States (Sep. 2012).
Cancelas, J.A., et al., "Connexin-43 gap junctions are involved in multiconnexin-expressing stromal support of hemopoietic progenitors and stem cells," Blood 96(2):498-505, Elsevier, Netherlands (Jul. 2000).
Ham, O., et al., "let-7b suppresses apoptosis and autophagy of human mesenchymal stem cells transplanted into ischemia/reperfusion injured heart 7by targeting caspase-3," Stem Cell Res Ther 6(1):147, BioMed Central, United Kingdom (Aug. 2015).
Mangione, C.M., et al., "Psychometric properties of the National Eye Institute Visual Function Questionnaire (NEI-VFQ)," Arch Ophthalmol 116(11):1496-1504, American Medical Association, United States (Nov. 1998).
Nasef, A., et al., "Selected Stro-1-enriched bone marrow stromal cells display a major suppressive effect on lymphocyte proliferation," Int J Lab Hematol 31(1):9-19, Wiley, United States (Feb. 2009).
(Continued)

*Primary Examiner* — Christopher M Babic
*Assistant Examiner* — Joel D Levin
(74) *Attorney, Agent, or Firm* — Sterne, Kessler, Goldstein & Fox P.L.L.C.

(57) ABSTRACT

The present disclosure provides a method of improving visual acuity in a subject suffering from an ocular disease. The method comprises administering to the subject a composition comprising mesenchymal lineage precursor or stem cells (MLPSCs) in an amount sufficient to improve visual acuity.

15 Claims, 5 Drawing Sheets

(56) References Cited

U.S. PATENT DOCUMENTS 10,550,369 B2 2/2020 Tom et al.
10,668,101 B2 6/2020 Aggarwal et al.
10,716,814 B2 7/2020 Aggarwal et al.
10,729,727 B2 8/2020 Aggarwal et al.
10,828,334 B1 11/2020 Aggarwal et al.
10,849,932 B2 12/2020 Itescu et al.
10,960,025 B2 3/2021 Aggarwal et al.
11,389,484 B2 7/2022 Aggarwal et al.
11,491,188 B2 11/2022 Itescu et al.
11,685,899 B2 6/2023 Simmons et al.
11,708,560 B2 7/2023 Tom et al.
11,795,435 B2 10/2023 Simmons et al.
11,821,004 B2 11/2023 Danilkovich et al.
12,115,194 B2 10/2024 Itescu et al.
12,215,352 B2 2/2025 Simmons et al.
12,410,405 B2 9/2025 Tom et al.
12,473,547 B2 11/2025 Brink et al.
2002/0044923 A1 4/2002 Mosca et al.
2003/0059412 A1 3/2003 Prockop et al.
2006/0280729 A1 12/2006 Mistry
2008/0132450 A1 6/2008 Lee
2008/0175825 A1 7/2008 Hampson et al.
2009/0214487 A1 8/2009 Varney et al.
2011/0200612 A1* 8/2011 Schuster ................ A61P 27/06 424/93.1
2016/0199413 A1 7/2016 Simonson et al.
2016/0271180 A1 9/2016 Yamashita
2017/0107495 A1 4/2017 Itescu et al.
2017/0340674 A1 11/2017 Itescu et al.
2018/0037867 A1 2/2018 Simmons et al.
2019/0240259 A1 8/2019 Aggarwal et al.
2020/0140822 A1 5/2020 Simmons et al.
2020/0197444 A1 6/2020 Danilkovitch et al.
2020/0231936 A1 7/2020 Tom et al.
2020/0345781 A1 11/2020 Honmou et al.
2021/0163932 A1 6/2021 Brink et al.
2021/0171913 A1 6/2021 Danilkovitch et al.
2022/0143097 A1 5/2022 Itescu
2022/0160776 A1 5/2022 Itescu et al.
2022/0226386 A1 7/2022 Itescu
2022/0275337 A1 9/2022 Devine et al.
2022/0364059 A1 11/2022 Bukulmez et al.
2023/0076630 A1 3/2023 Aggarwal et al.
2023/0089901 A1 3/2023 Danilkovich et al.
2023/0097931 A1 3/2023 Itescu
2023/0104108 A1 4/2023 Itescu
2023/0165904 A1 6/2023 Itescu
2023/0172991 A1 6/2023 Itescu
2023/0220349 A1 7/2023 Simmons
2023/0293589 A1 9/2023 Itescu
2023/0293590 A1 9/2023 Itescu et al.
2023/0346846 A1 11/2023 Itescu et al.
2023/0398154 A1 12/2023 Itescu et al.
2024/0041934 A1 2/2024 Itescu et al.
2024/0091266 A1 3/2024 Itescu et al.
2024/0117315 A1 4/2024 Tom et al.
2024/0197787 A1 6/2024 Itescu
2024/0207323 A1 6/2024 Itescu
2025/0032552 A1 1/2025 Itescu
2025/0090589 A1 3/2025 Itescu et al.
2025/0129337 A1 4/2025 Simmons et al.
2025/0161365 A1 5/2025 Itescu et al.
2025/0312379 A1 10/2025 Danilkovich et al.
2025/0319428 A1 10/2025 Horst et al.

FOREIGN PATENT DOCUMENTS

ES 2385450 T3 7/2012
JP 2009500297 A 1/2009
KR 20130050939 A 5/2013
KR 20200015174 A 2/2020
WO WO-9201070 A1 1/1992
WO WO-9303769 A1 3/1993
WO WO-9426877 A1 11/1994
WO WO-2004085630 A1 10/2004
WO WO-2005093044 A1 10/2005
WO WO-2006108229 A1 10/2006
WO WO-2006133052 A2 12/2006
WO WO-2006136244 A2 12/2006
WO WO-2007087139 A2 8/2007
WO WO-2008006168 A1 1/2008
WO WO-2008042174 A2 4/2008
WO WO-2008116157 A2 9/2008
WO WO-2010005527 A1 1/2010
WO WO-2010019886 A1 2/2010
WO WO-2011129461 A1 10/2011
WO WO-2011139357 A1 11/2011
WO WO-2012048093 A2 4/2012
WO WO-2015016761 A2 2/2015
WO WO-2016102601 A1 6/2016
WO WO-2016139340 A1 9/2016
WO WO-2017132358 A1 8/2017
WO WO-2019051623 A1 3/2019
WO WO-2019102268 A1 5/2019
WO WO-2020141473 A1 7/2020
WO WO-2020141483 A1 7/2020
WO WO-2020157660 A1 8/2020
WO WO-2020234450 A1 11/2020
WO WO-2021024207 A1 2/2021

OTHER PUBLICATIONS

Co-pending U.S. Appl. No. 17/836,786, inventors Aggarwal, S., et al., filed Jun. 9, 2022 (Not yet Published).
Co-pending U.S. Appl. No. 17/633,063, inventor Devine, D., et al., filed Aug. 5, 2020 (Not yet Published).
Co-pending U.S. Appl. No. 17/612,939, inventor Itescu, S., et al., filed May 22, 2020 (Not yet Published).
Co-pending U.S. Appl. No. 63/365,393, inventor Horst, J., et al., filed May 26, 2022 (Not yet Published).
Bornstein, M.B., et al., "A Placebo-controlled, Double-blind, Randomized, Two-center, Pilot Trial of Cop 1 in Chronic Progressive Multiple Sclerosis," Neurology 41(4):533-539, Lippincott Williams & Wilkins, United States (Apr. 1991).
Buchschacher, G.L. and Panganiban, A.T., "Human Immunodeficiency Virus Vectors for Inducible Expression of Foreign Genes," Journal of Virology 66(5):2731-2739, American Society For Microbiology, United States (May 1992).
Burns, J.C., et al., "Vesicular Stomatitis Virus G Glycoprotein Pseudotyped Retroviral Vectors: Concentration to Very High Titer and Efficient Gene Transfer Into Mammalian and Nonmammalian Cells," Proceedings of the National Academy of Sciences of the United States of America 90(17):8033-8037, National Academy of Sciences, United States (Sep. 1993).
Chinnadurai, R., et al., "Cryopreserved Mesenchymal Stromal Cells Are Susceptible to T-Cell Mediated Apoptosis Which Is Partly Rescued by IFNγ Licensing," Stem Cells 34(9):2429-2442, Oxford University Press, England (Sep. 2016).
Dang, Y., et al., "Stem Cell Therapies for Age-related Macular Degeneration: the Past, Present, and Future," Clinical Interventions in Aging 10:255-264, Dove Medical Press, New Zealand (Jan. 2015).
Fisher-Hoch, S.P., et al., "Protection of Rhesus Monkeys From Fatal Lassa Fever by Vaccination With a Recombinant Vaccinia Virus Containing the Lassa Virus Glycoprotein Gene," Proceedings of the National Academy of Sciences of the United States of America 86(1):317-321, National Academy of Sciences, United States (Jan. 1989).
Francois, M., et al., "Cryopreserved Mesenchymal Stromal Cells Display Impaired Immunosuppressive Properties as a Result of Heat-shock Response and Impaired Interferon-γ Licensing," Cytotherapy 14(2):147-152, Elsevier, England (Feb. 2012).
Gronthos, S. and Simmons, P.J., "The Growth Factor Requirements of STRO-1-positive Human Bone Marrow Stromal Precursors Under Serum-deprived Conditions in Vitro," Blood 85(4):929-940, Elsevier, United States (Feb. 1995).
Gronthos, S., et al., "Molecular and Cellular Characterisation of Highly Purified Stromal Stem Cells Derived From Human Bone

(56) References Cited

OTHER PUBLICATIONS

Marrow," Journal of Cell Science 116(Pt 9):1827-1835, Company of Biologists, England (May 2003).
Higuchi, A., et al., "Stem Cell Therapies for Reversing Vision Loss," Trends in Biotechnology 35(11):1102-1117, Elsevier Science Publishers, England (Nov. 2017).
International Search Report and Written Opinion for Application No. PCT/IB2020/050032, European Patent Office, Netherlands, mailed on Mar. 16, 2020, 10 pages.
Johann, S.V., et al., "GLVR1, a Receptor for Gibbon Ape Leukemia Virus, is Homologous to a Phosphate Permease of Neurospora Crassa and is Expressed at High Levels in the Brain and Thymus," Journal of Virology 66(3):1635-1640, American Society For Microbiology, United States (Mar. 1992).
Kotin, R.M., "Prospects for The Use of Adeno-Associated Virus as a Vector for Human Gene Therapy," Human Gene Therapy 5(7):793-801, Mary Ann Liebert Inc, United States (Jul. 1994).
Lebkowski, J.S., et al., "Adeno-associated Virus: a Vector System for Efficient Introduction and Integration of Dna Into a Variety of Mammalian Cell Types," Molecular and cellular biology 8(10):3988-3996, American Society for Microbiology, United States (Oct. 1988).
Lund, R., et al., "Cell Transplantation as a Treatment for Retinal Disease," Progress in Retinal and Eye Research 20(4):415-449, Pergamon Press, England (Jul. 2001).
Mangione, C.M., et al., "Development of the 25-item National Eye Institute Visual Function Questionnaire," Archives of Ophthalmology 119(7):1050-1058, American Medical Association, United States (Jul. 2001).
Miller, A.D. and Rosman, G.J., "Improved Retroviral Vectors for Gene Transfer and Expression," BioTechniques 7(9):980-990, Future Science, England (Oct. 1989).
Miller, A.D., et al., "Construction and Properties of Retrovirus Packaging Cells Based on Gibbon Ape Leukemia Virus," Journal of Virology 65(5):2220-2224, American Society For Microbiology, United States (May 1991).
Miller, A.D., et al., "Retrovirus Packaging Cells," Human Gene Therapy 1(1): 5-14, Liebert, United States (1990).
Muzyczka, N., "Use of Adeno-Associated Virus as a General Transduction Vector for Mammalian Cells," Current Topics in Microbiology and Immunology 158:97-129, Springer Verlag, Germany (1992).
Scarpa, M., et al., "Characterization of Recombinant Helper Retroviruses From Moloney-based Vectors in Ecotropic and Amphotropic Packaging Cell Lines," Virology 180(2):849-852, Academic Press, United States (Feb. 1991).
Suner, I., et al., "Responsiveness of Nei Vfq-25 to Changes in Visual Acuity in Neovascular Amd: Validation Studies From Two Phase 3 Clinical Trials, "Investigative Ophthalmology & Visual Science 50(8):3629-3635, Association For Research In Vision And Ophthalmology, United States (Aug. 2009).
Wilson, C., et al., "Formation of Infectious Hybrid Virions With Gibbon Ape Leukemia Virus and Human T-Cell Leukemia Virus Retroviral Envelope Glycoproteins and the Gag and Pol Proteins of Moloney Murine Leukemia Virus," Journal of Virology 63(5):2374-2378, American Society For Microbiology, United States (May 1989).
Zannettino, A.C., et al., "The Sialomucin CD164 (MGC-24v) is an Adhesive Glycoprotein Expressed by Human Hematopoietic Progenitors and Bone Marrow Stromal Cells That Serves as a Potent Negative Regulator of Hematopoiesis," Blood 92(8):2613-2628, Elsevier, United States (Oct. 1998).
International Search Report and Written Opinion for International Application No. PCT/EP2021/058683, European Patent Office, Netherlands, mailed Jun. 14, 2021, 10 pages.
Wang, L.T., et al., "Human mesenchymal stem cells (MSCs) for treatment towards immune- and inflammation-mediated diseases: review of current clinical trials," J Biomed Sci 23(1):76, BioMed Central Ltd., United Kingdom (Nov. 2016).
International Search Report and Written Opinion for International Application No. PCT/IB2021/055055, European Patent Office, Netherlands, mailed Sep. 17, 2021, 10 pages.
Dos Santos, F., et al., "Toward a clinical-grade expansion of mesenchymal stem cells from human sources: a microcarrier-based culture system under xeno-free conditions," Tissue Eng Part C Methods 17(12):1201-1210, Mary Ann Liebert Inc., United States (Dec. 2011).
International Search Report and Written Opinion for International Application No. PCT/IB2023/062429, European Patent Office, Netherlands, mailed Mar. 5, 2024, 12 pages.
Pereira, T., et al., "MSCs conditioned media and umbilical cord blood plasma metabolomics and composition," PLoS One 9(11):e113769, Public Library of Science, United States (Nov. 2014).
Eisenberg, C.A., et al., "Establishment of the mesodermal cell line QCE-6. A model system for cardiac cell differentiation," Circ Res 78(2):205-216, Lippincott Williams and Wilkins Ltd., United States (Feb. 1996).
R&D Systems, "Newborn Calf Serum S11250:R&D Systems," accessed at https://www.rndsystems.com/products/newborn-calf-serum_s11250.
Pilgrim, C.R., et al., "A Review of Fetal Bovine Serum in the Culture of Mesenchymal Stromal Cells and Potential Alternatives for Veterinary Medicine," Front Vet Sci 9:859025, Frontiers Media SA, Switzerland (May 2022).
International Search Report and Written Opinion for International Application No. PCT/IB2021/057314, European Patent Office, Netherlands, mailed Oct. 22, 2021, 10 pages.
Martire, A., et al., "Mesenchymal stem cells attenuate inflammatory processes in the heart and lung via inhibition of TNF signaling," Basic Res Cardiol 111(5):54, D. Steinkopff-Verlag, Germany (Sep. 2016).
Yan, L., et al., "Critical Role of Tumor Necrosis Factor Signaling in Mesenchymal Stem Cell-Based Therapy for Autoimmune and Inflammatory Diseases," Front Immunol 9:1658, Frontiers Media SA, Switzerland (Jul. 2018).
Burand, A.J., et al., "Function of Cryopreserved Mesenchymal Stromal Cells With and Without Interferon-γ Prelicensing is Context Dependent," Stem Cells 35(5):1437-1439, Oxford University Press, United States (May 2017).
Co-pending U.S. Appl. No. 18/484,347, inventor Danilkovitch, A., et al., filed Oct. 10, 2023 (Not yet Published).
Co-pending U.S. Appl. No. 18/711,167, inventor Itescu, S., et al., filed Nov. 17, 2022 (Not yet Published).
Hobbs, S.D., et al., "Wet Age-Related Macular Degeneration (AMD)," StatPearls [Internet], accessed at https://www.ncbi.nlm.nih.gov/books/NBK572147/, last updated Aug. 11, 2024, 30 pages.
Co-pending U.S. Appl. No. 18/872,445, inventor Itescu, S., filed Jun. 8, 2023 (Not yet Published).
Co-pending U.S. Appl. No. 18/880,992, inventor Itescu, S., et al., filed Jan. 3, 2025 (Not yet Published).
Co-pending U.S. Appl. No. 19/137,213, inventor Itescu, S., et al., filed Jun. 9, 2025 (Not yet Published).
Co-pending U.S. Appl. No. 19/137,193, inventor Itescu, S., et al., filed Jun. 9, 2025 (Not yet Published).
Co-pending U.S. Appl. No. 19/136,677, inventor Itescu, S., et al., filed Jun. 6, 2025 (Not yet Published).
Co-pending U.S. Appl. No. 19/136,773, inventor Itescu, S., et al., filed Jun. 6, 2025 (Not yet Published).
Co-pending U.S. Appl. No. 19/293,945, inventor Tom, S., et al., filed Jul. 8, 2025 (Not yet Published).
Co-pending U.S. Appl. No. 19/482,552, inventor Davidzon, N., filed Nov. 7, 2025 (Not yet Published).
Co-pending U.S. Appl. No. 19/388,629, inventors Danilkovich, A., et al., filed Nov. 13, 2025(Not yet Published).
Li, X., et al., "Immunomodulatory effects of mesenchymal stem cells in peripheral nerve injury," Stem Cell Research & Therapy. 13:18, BioMed Central, United Kingdom (Jan. 2022).

* cited by examiner

METHOD FOR IMPROVING VISUAL ACUITY

CROSS-REFERENCE TO RELATED APPLICATIONS

This application is the U.S. National Phase of International Application No. PCT/IB2020/050032, filed on Jan. 3, 2020, which claims the priority benefit of U.S. Provisional Application No. 62/788,037, filed on Jan. 3, 2019, each of which is incorporated herein in its entirety.

TECHNICAL FIELD

The present disclosure relates to cellular therapy products comprising mesenchymal lineage precursor or stem cells for improving visual acuity.

BACKGROUND

As a complex and sensitive organ of the body, the eye can experience numerous diseases and other deleterious conditions that affect its ability to function normally. Many of these conditions are associated with damage or degeneration of specific ocular cells, and tissues made up of those cells. As one example, diseases and degenerative conditions of the optic nerve and retina are the leading causes of blindness throughout the world. Damage or degeneration of the cornea, lens and associated ocular tissues represent another significant cause of vision loss. The retina contains seven layers of alternating cells and processes that convert a light signal into a neural signal. The retinal photoreceptors and adjacent retinal pigment epithelium (RPE) form a functional unit that, in many disorders, becomes unbalanced due to genetic mutations or environmental conditions (including age). This results in loss of photoreceptors: through apoptosis or secondary degeneration, which leads to progressive deterioration of vision and, in some instances, to blindness (for a review, see, e.g., Lund, R. D. et al., 2001, Progress in Retinal and Eye Research 20: 415-449). Two classes of ocular disorders that fall into this pattern are age-related macular degeneration (AMD) and retinitis pigmentosa (RP).

Although therapeutic agents, including anti-VEGF agents such as Lucentis®, have been used for treating conditions such as wet neovascular AMD where excessive VEGF production results in abnormal leaky vasculature and extravascular fluid accumulation, there is a need for therapeutic treatments that are effective in directly improving visual acuity in patients with diseases and degenerative conditions of the optic nerve.

SUMMARY OF THE DISCLOSURE

The present disclosure relates to use of an off-the-shelf ex vivo expanded allogeneic mesenchymal lineage precursor or stem cell (MLPSC) product for improving visual acuity in a patient suffering from an ocular disorder.

Accordingly, the present disclosure provides a method of improving visual acuity in a subject suffering from an ocular disease, the method comprising administering to the subject a composition comprising mesenchymal lineage precursor or stem cells (MLPSCs) in an amount sufficient to improve visual acuity.

In one embodiment, the ocular disease is associated with inflammation or degradation of the optic nerve.

In another embodiment, the ocular disease is associated with inflammation or degradation of the optic nerve photoreceptors.

In another embodiment, the subject has previously been treated with an anti-VEGF agent in order to reduce neovascularization, abnormal leaky vasculature and extravascular fluid accumulation in the optic tissue.

In another embodiment, the subject has been treated with a monthly dosage of anti-VEGF agent for at least 1 month, or at least 2 months, or at least 3 months.

In another embodiment, the agent is an anti-VEGF antibody or fragment thereof. For example, the anti-VEGF agent may be Lucentis®.

In another embodiment, the mesenchymal lineage precursor or stem cells are isolated by immunoselection.

In one embodiment, the isolated population of cells comprises culture-expanded mesenchymal lineage precursor or stem cells. In an alternate embodiment, the isolated population of cells comprises freshly isolated mesenchymal lineage precursor or stem cells.

In one embodiment, the MLPSCs are isolated by immunoselection. In one embodiment, the cells have been immunoselected for expression of TNAP. In one embodiment, the immunoselected cells co-express TNAP and STRO-1. In one embodiment, the immunoselected cells co-express TNAP and STRO-$1^{bright}$. In one embodiment the immunoselected cells are culture expanded prior to administration.

In one embodiment the MLPSCs are mesenchymal stem cells. In on embodiment the mesenchymal stem cells are culture expanded prior to administration.

In one embodiment, the MLPSCs comprise at least 5%, or at least 10%, or at least 20%, or at least 50%, or at least 60%, or at least 70%, or at least 80%, or at least 90%, or a least 95%, or 100% of the total cell population of the composition.

In one embodiment, the composition comprises MLPSCs and a cryopreservative.

In one embodiment the cryopreservative in the composition is DMSO or Profreeze®.

In one embodiment the composition comprises MLPSCs in 42.5% (v/v) Profreeze®/50% αMEM (v/v)/7.5% (v/v) DMSO.

In another embodiment, the MLPSCs are administered to the subject at a dose of less than 350,000 cells, or less than 250,000 cells, or less than 100,000 cells, or less than 95,000 cells, or less than 90,000 cells or less than 80,000 cells, or less than 75,000 cells, or less than 70,000 cells.

In another embodiment, the MLPSCs are administered to the subject at a dose of less than 100,000 cells per mL of vitreous humor, or less than 75,000 cells per mL of vitreous humor, or less than 50,000 cells per mL of vitreous humor, or less than 25,000 cells per mL of vitreous humor, less than 20,000 cells per mL of vitreous humor.

In another embodiment, the MLPSCs are administered to the subject at a dose of about 24,500 MPCs per mL of vitreous humor.

In another embodiment, the MLPSCs are administered as a single dose.

In another embodiment, the MLPSCs are administered intravitreally. For example, the MLPSCs may be administered by intravitreal injection.

In another embodiment, administration of the MLPSCs results in at least a 10-point improvement from baseline in composite NEI VFQ-25 score over at least a 3 month period, or at least a 6 month period, or at least a 12 month period, or at least an 18 month period, or at least a 24 month period.

In another embodiment, administration of the MLPSCs results in an reduction in optical coherence tomograph (OCT) within a 3 month period.

DESCRIPTION OF EMBODIMENTS

General Techniques and Definitions

Figures 1A, 1B, 1C, 1D:
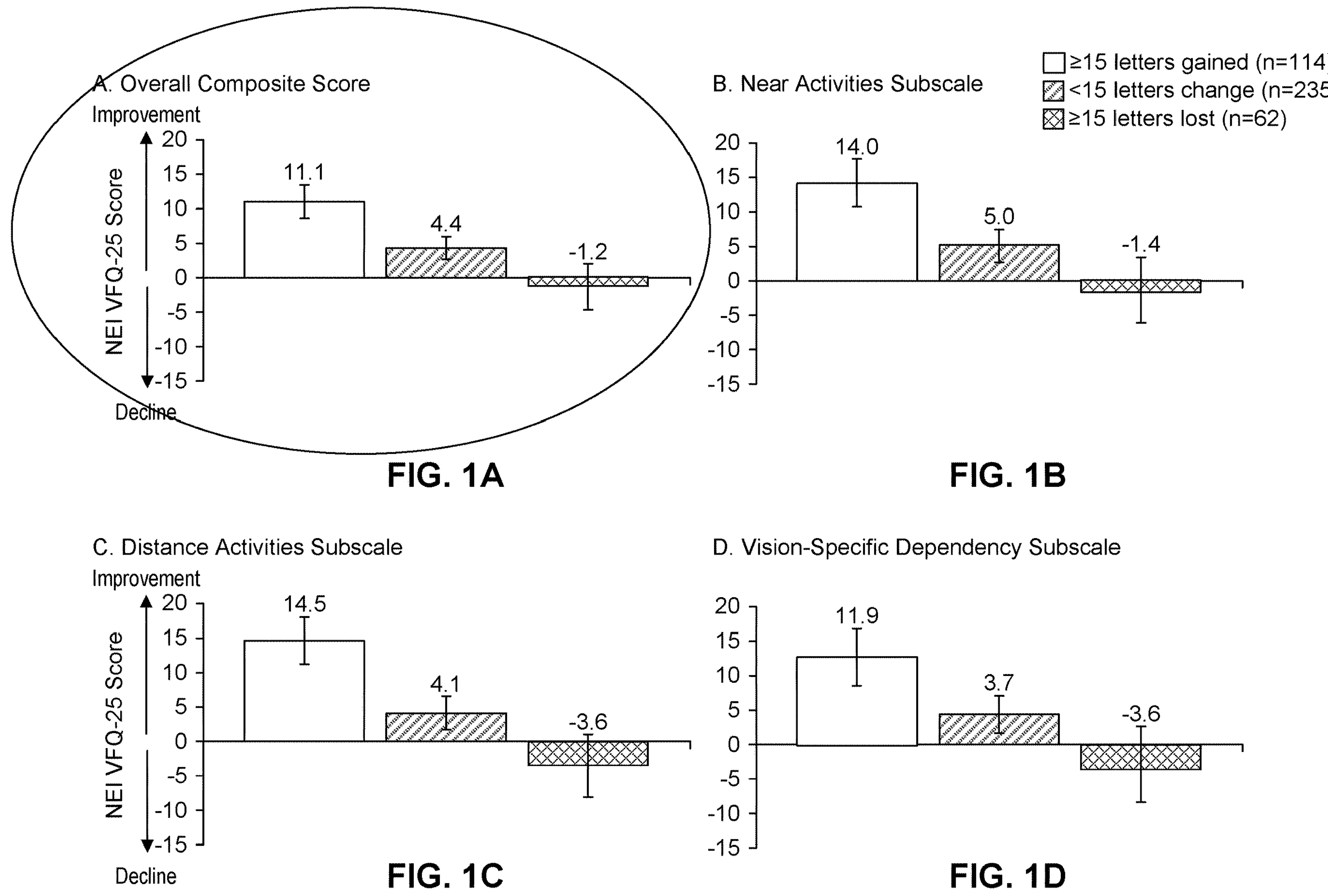
FIGS. 1A-1D are from "Responsiveness of NEI VFQ-25 to Changes in Visual Acuity in Neovascular AMD: Validation Studies from Two Phase 3 Clinical Trials" (Invest. Opthalmol. Vis. Sci. 2009; 50(8)3629-3635. doi:10.1167/iovs.08-3225.) ANCHOR: the least-squares mean change in NEI VFQ-25 scores for patients who gained ≥15 letters, gained or lost <15 letters, and lost ≥15 letters for the overall composite score (1A) and the three pre-specified subscales: near activities (1B), distance activities (1C), and vision-specific dependency (1D) at 12 months. Error bars represent 95%

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, group of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise indicated, the stem cells, cell culture, and surgical techniques utilized in the present disclosure are standard procedures, well known to those skilled in the art. Such techniques are described and explained throughout the literature in sources such as Perbal, 1984; Sambrook & Green, 2012; Brown, 1991; Glover & Hames, 1995 and 1996; Ausubel., 1987 including all updates until present; Harlow & Lane, 1988; and Coligan et al., 1991 including all updates until present.

As used in this specification and the appended claims, terms in the singular and the singular forms "a," "an" and "the," for example, optionally include plural referents unless the content clearly dictates otherwise.

The term "subject" as used herein refers to a mammal including human and non-human animals. More particularly, the mammal is a human. Terms such as "subject", "patient" or "individual" are terms that can, in context, be used interchangeably in the present disclosure. In certain examples, the subject may be an adult or a child (pediatric) subject.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is used to refer to an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Mesenchymal Lineage Precursor or Stem Cells

As used herein, the term "mesenchymal lineage precursor or stem cells" refers to undifferentiated multipotent cells that have the capacity to self-renew while maintaining multipotency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells.

The term "mesenchymal lineage precursor or stem cells" includes both parent cells and their undifferentiated progeny. The term also includes mesenchymal precursor cells (MPC), multipotent stromal cells, mesenchymal stem cells, perivascular mesenchymal precursor cells, and their undifferentiated progeny.

Mesenchymal lineage precursor or stem cells can be autologous, allogeneic, xenogeneic, syngeneic or isogeneic. Autologous cells are isolated from the same individual to which they will be reimplanted. Allogeneic cells are isolated from a donor of the same species. Xenogeneic cells are isolated from a donor of another species. Syngeneic or isogeneic cells are isolated from genetically identical organisms, such as twins, clones, or highly inbred research animal models.

Mesenchymal lineage precursor or stem cells reside primarily in the bone marrow, but have also been shown to be present in diverse host tissues including, for example, cord blood and umbilical cord, adult peripheral blood, adipose tissue, trabecular bone and dental pulp.

Mesenchymal lineage precursor or stem cells can be isolated from host tissues and enriched for by immunoselection. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in Simmons & Torok-Storb, 1991.

STRO-1+ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

The term "enriched" as used herein describes a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, for example, CFU-F (fibroblasts) or a subset thereof (e.g., 50% or 60% or 70% or 70% or 90% or 95%) can have this activity. In one example, a population enriched for TNAP+ cells comprises at least about 0.1% or 0.5% or 1% or 2% or 5% or 10% or 15% or 20% or 25% or 30% or 50% or 75% TNAP+ cells. In this regard, the term "population of cells enriched for TNAP+ cells" will be taken to provide explicit support for the term "population of cells comprising X % TNAP+ cells", wherein X % is a percentage as recited herein. In one example, a population enriched for STRO-1+ and TNAP+ cells comprises at least about 0.1% or 0.5% or 1% or 2% or 5% or 10% or 15% or 20% or 25% or 30% or 50% or 75% STRO-1+ and TNAP+ cells. In this regard, the term "population of cells enriched for STRO-1+ and TNAP+ cells" will be taken to provide explicit support for the term "population of cells comprising X % STRO-1+ and TNAP+ cells", wherein X % is a percentage as recited herein.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., MPCs) expressing STRO-2 and/or STRO-3 (TNAP) and/or STRO-4 and/or VCAM-1 and/or CD146 and/or 3G5 also express STRO-1 (and can be STRO-1$^{bright}$). Accordingly, an indication that cells are STRO-1+ does not mean that the cells are selected by STRO-1 expression. In one example, the cells are selected based on at least STRO-3 expression, e.g., they are STRO-3+ (TNAP+).

Reference to selection of a cell or population thereof does not necessarily require selection from a specific tissue source. As described herein, STRO-1+ cells can be selected from or isolated from or enriched from a large variety of sources. That said, in some examples, these terms provide support for selection from any tissue comprising STRO-1+ cells or vascularized tissue or tissue comprising pericytes (e.g., STRO-1+ pericytes) or any one or more of the tissues recited herein.

In one example, the mesenchymal lineage precursor or stem cells of the disclosure express one or more markers individually or collectively selected from the group consisting of TNAP+, VCAM-1+, THY-1+, STRO-2+, STRO-4+ (HSP-90β), CD45+, CD146+, 3G5+.

By "individually" is meant that the disclosure encompasses the recited markers or groups of markers separately, and that, notwithstanding that individual markers or groups of markers may not be separately listed herein, the accompanying claims may define such marker or groups of markers separately and divisibly from each other.

By "collectively" is meant that the disclosure encompasses any number or combination of the recited markers or groups of markers, and that, notwithstanding that such numbers or combinations of markers or groups of markers may not be specifically listed herein, the accompanying claims may define such combinations or sub-combinations separately and divisibly from any other combination of markers or groups of markers.

A cell that is referred to as being "positive" for a given marker may express either a low (lo or dim or dull), intermediate (median) or a high (bright, bri) level of that marker depending on the degree to which the marker is present on the cell surface, where the terms relate to intensity of fluorescence or other marker used in the sorting process of the cells or flow cytometric analysis of the cells. The distinction of low (lo or dim or dull), intermediate (median), or high (bright, bri) will be understood in the context of the marker used on a particular cell population being sorted or analysed. A cell that is referred to as being "negative" for a given marker is not necessarily completely absent from that cell. This term means that the marker is expressed at a relatively very low level by that cell, and that it generates a very low signal when detectably labeled or is undetectable above background levels, for example, levels detected using an isotype control antibody.

The term "bright" or bri as used herein, refers to a marker on a cell surface that generates a relatively high signal when detectably labeled. Whilst not wishing to be limited by theory, it is proposed that "bright" cells express more of the target marker protein (for example, the antigen recognized by a STRO-1 antibody) than other cells in the sample. For instance, STRO-$1^{bri}$ cells produce a greater fluorescent signal, when labeled with a FITC-conjugated STRO-1 antibody as determined by fluorescence activated cell sorting (FACS) analysis, than non-bright cells (STRO-$1^{lo/dim/dull/intermediate/median}$). In one example, the mesenchymal lineage precursor or stem cells are isolated from bone marrow and enriched for by selection of STRO-1+ cells. In this example, "bright" cells constitute at least about 0.1% of the most brightly labeled bone marrow mononuclear cells contained in the starting sample. In other examples, "bright" cells constitute at least about 0.1%, at least about 0.5%, at least about 1%, at least about 1.5%, or at least about 2%, of the most brightly labeled bone marrow mononuclear cells contained in the starting sample. In an example, STRO-$1^{bright}$ cells have 2 log magnitude higher expression of STRO-1 surface expression relative to "background", namely cells that are STRO-1-. By comparison, STRO-$1^{l/dim/dull}$ and/or STRO-$1^{intermediate/median}$ cells have less than 2 log magnitude higher expression of STRO-1 surface expression, typically about 1 log or less than "background".

In one example, the STRO-1+ cells are STRO-$1^{bright}$. In one example, the STRO-$1^{bright}$ cells are preferentially enriched relative to STRO-$1^{lo/dim/dull}$ or STRO-$1^{intermediate/median}$ cells.

In one example, the STRO-$1^{bright}$ cells are additionally one or more of TNAP+, VCAM-1+, THY-1+, STRO-2+, STRO-4+ (HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the STRO-$1^{bright}$ cells are perivascular mesenchymal precursor cells as defined in WO 2004/85630, characterized by the presence of the perivascular marker 3G5.

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ cells are capable of differentiation into at least two different germ lines. Non-limiting examples of the lineages to which the cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In one example, the mesenchymal lineage precursor or stem cells are mesenchymal stem cells (MSCs). The MSCs may be a homogeneous composition or may be a mixed cell population enriched in MSCs. Homogeneous MSC compositions may be obtained by culturing adherent bone marrow or periosteal cells, and the MSCs may be identified by specific cell surface markers which are identified with unique monoclonal antibodies. A method for obtaining a cell population enriched in MSCs using plastic adherence technology is described, for example, in U.S. Pat. No. 5,486,359. MSC prepared by conventional plastic adherence isolation relies on the non-specific plastic adherent properties of CFU-F. Alternative sources for MSCs include, but are not limited to, blood, skin, cord blood, muscle, fat, bone, and perichondrium.

The mesenchymal lineage precursor or stem cells may be cryopreserved prior to administration to a subject.

In a preferred embodiment of the invention, the mesenchymal lineage precursor or stem cells are obtained from a master cell bank derived from mesenchymal lineage precursor or stem cells enriched from the bone marrow of healthy volunteers. The use of mesenchymal lineage precursor or stem cells derived from such a source is particularly advantageous for subjects who do not have an appropriate family member available who can serve as the mesenchymal lineage precursor or stem cell donor, or are in need of immediate treatment and are at high risk of relapse, disease-related decline or death, during the time it takes to generate mesenchymal lineage precursor or stem cells.

The present inventors have shown that mesenchymal precursor cells of the disclosure have unexpectedly high potency in terms of their ability to inhibit T cell proliferation after cryopreservation and thawing. In contrast, prior publications teach that cryopreserved mesenchymal stem cells display impaired immunosuppressive properties following thawing (Francois et al., 2012; Chinnadurai et al., 2016).

The isolated or enriched mesenchymal lineage precursor or stem cells can be expanded ex vivo or in vitro by culture. As will be appreciated by those skilled in the art, the isolated or enriched mesenchymal lineage precursor or stem cells can be cryopreserved, thawed and subsequently or further expanded ex vivo or in vitro by culture.

The cultured mesenchymal lineage precursor or stem cells are phenotypically different to cells in vivo. For example, in one embodiment they express one or more of the following markers, CD44, NG2, DC146 and CD140b.

The cultured mesenchymal lineage precursor or stem cells are biologically different to cells in vivo, having a higher rate of proliferation compared to the largely non-cycling (quiescent) cells in vivo.

In one example, a population of cells enriched for mesenchymal lineage precursor or stem cells is seeded at about 6000 to 7000 viable cells/$cm^2$ in serum-supplemented culture medium, for example, Dulbecco's Modified Eagle medium (DMEM) supplemented with 10% fetal bovine serum (FBS) and 2 mM glutamine, and allowed to adhere to the culture vessel overnight at 37° C., 20% $O_2$. In an embodiment, the cells are seeded at about 6000, 6100, 6200, 6300, 6400, 6500, 6600, 6700, 6800, 6810, 6820, 6830, 6840, 6850, 6860, 6870, 6880, 6890, 6890, 6900, 6910, 6920, 6930, 6940, 6970, 6980, 6990, or 7000 viable cells/$cm^2$, preferably at about 6850 to 6860 viable cells/$cm^2$. The culture medium is subsequently replaced and the cells cultured for a total of 68 to 72 hours at 37° C., 5% $O_2$ prior to co-culturing with T cells and determining the amount of IL-2Rα expressed by the T cells.

Compositions and Administration

A composition comprising mesenchymal lineage precursor or stem cells may be prepared in a pharmaceutically acceptable carrier. The term "pharmaceutically acceptable carrier" as used herein refers to compositions of matter that facilitate the storage, administration, and/or maintain the biological activity of the mesenchymal lineage precursor or stem cells.

In one example, the carrier does not produce significant local or systemic adverse effect in the recipient. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, scaffolds, isotonic and absorption delaying agents that do not affect the viability and activity of the mesenchymal lineage precursor or stem cells. The selection of a suitable carrier is within the skill of those skilled in the art.

Compositions of the disclosure may conveniently be presented in unit dosage form and may be prepared by any of the methods well known in the art. The term "dosage unit form" as used herein refers to physically discrete units suited as unitary dosages for subjects to be treated; each unit containing a predetermined quantity of active compound calculated to produce the desired therapeutic or prophylactic effect in association with the pharmaceutical carrier. The dose of mesenchymal lineage precursor or stem cells may vary according to factors such as the disease state, age, sex, and weight of the subject to be treated.

The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the cell population of the composition.

Compositions of the disclosure may be cryopreserved. Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cyropreservation solution may comprise a sterile, non-pyrogenic isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, USP ($C_2H_3NaO_2.3H_2O$); 37 mg of potassium chloride, USP (KCl); and 30 mg of magnesium chloride, USP ($MgCl_2.6H_2O$). It contains no antimicrobial agents. The pH is adjusted with sodium hydroxide. The pH is 7.4 (6.5 to 8.0).

The cryopreservation solution may comprise Profreeze™. The cryopreservation solution may additionally or alternatively comprise culture medium.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methycellulose, polyvinyl pyrrolidone (PVP) and trehalose.

In one embodiment, cells are suspended in 42.5% Profreeze™/50% αMEM/7.5% DMSO and cooled in a controlled-rate freezer.

The cryopreserved composition may be thawed and administered directly to the subject. Alternatively, the cryopreserved composition may be thawed and the mesenchymal lineage precursor or stem cells resuspended in an alternate carrier prior to administration.

Genetically-Modified Cells

In one embodiment, the mesenchymal lineage precursor or stem cells are genetically unmodified. In one embodiment, the mesenchymal lineage precursor or stem cells are genetically modified, for example, to express and/or secrete a protein of interest, for example, a protein providing a therapeutic and/or prophylactic benefit.

Methods for genetically modifying a cell will be apparent to the skilled person. For example, a nucleic acid that is to be expressed in a cell is operably-linked to a promoter for inducing expression in the cell. For example, the nucleic acid is linked to a promoter operable in a variety of cells of a subject, such as, for example, a viral promoter, for example, a CMV promoter (e.g., a CMV-IE promoter) or a SV-40 promoter. Additional suitable promoters are known in the art.

Preferably, the nucleic acid is provided in the form of an expression construct. The term "expression construct" as used herein refers to a nucleic acid that has the ability to confer expression on a nucleic acid (e.g., a reporter gene and/or a counter-selectable reporter gene) to which it is operably connected, in a cell. Within the context of the present disclosure, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled person and are described, for example, in Ausubel F. M., 1987 including all updates until present; or Sambrook & Green, 2012. For example, each of the components of the expression construct is amplified from a suitable template nucleic acid using, for example, PCR and subsequently cloned into a suitable expression construct, such as, for example, a plasmid or a phagemid.

Vectors suitable for such an expression construct are known in the art and/or described herein. For example, an expression vector suitable for the method of the present invention in a mammalian cell is, for example, a vector of the pcDNA vector suite (Invitrogen), a vector of the pCI vector suite (Promega), a vector of the pCMV vector suite (Clontech), a pM vector (Clontech), a pSI vector (Promega), a VP 16 vector (Clontech), or a vector of the pcDNA vector suite (Invitrogen).

The skilled person will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., International publication WO1994/026877; Buchschacher & Panganiban, 1992; Johann et al., 1992; Sommerfelt & Weiss, 1990; Wilson et al., 1989; Miller et al., 1991; Lynch, et al., 1991; Miller & Rosman, 1989; Miller, 1990; Scarpa et al., 1991; Burns et al., 1993.

Various adeno-associated virus (AAV) vector systems have also been developed for nucleic acid delivery. AAV vectors can be readily constructed using techniques known in the art. (see, e.g., U.S. Pat. Nos. 5,173,414 and 5,139,941; International publications WO 92/01070 and WO 93/03769; Lebkowski et al., 1988; Vincent et al., 1990; Carter, 1992; Muzyczka, 1992; Kotin, 1994; Shelling & Smith, 1994; Zhou et al., 1994.

Additional viral vectors useful for delivering an expression construct of the invention include, for example, those derived from the pox family of viruses, such as vaccinia virus and avian poxvirus or an alphavirus or a conjugate virus vector (e.g., that described in Fisher-Hoch et al., 1989.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

EXAMPLES

Example 1 Materials and Methods

Mesenchymal Lineage Precursor or Stem Cells (MLPSCs) Prepared Using Plastic Adherence Techniques MLPSCs were generated de novo from bone marrow as described in U.S. Pat. No. 5,837,539. Approximately 80-100 ml of bone marrow was aspirated into sterile heparin-containing syringes and taken to the MDACC Cell Therapy Laboratory for MSC generation. The bone marrow mononuclear cells were isolated using ficoll-hypaque and placed into two T175 flask with 50 ml per flask of MLPSC expansion medium which includes alpha modified MEM (αMEM) containing gentamycin, glutamine (2 mM) and 20% (v/v) fetal bovine serum (FBS) (Hyclone). The cells were cultured for 2-3 days in 37° C., 5% $CO_2$ at which time the non-adherent cells were removed; the remaining adherent cells were continually cultured until the cell confluence reached 70% or higher (7-10 days), and then the cells were trypsinized and replaced in six T175 flasks with expansion medium (50 ml of medium per flask).

Immunoselection of Mesenchymal Lineage Precursor or Stem Cells (MLPSCs)

Bone marrow (BM) was harvested from healthy normal adult volunteers (20-35 years old). Briefly, 40 ml of BM is aspirated from the posterior iliac crest into lithium-heparin anticoagulant-containing tubes.

Bone marrow mononuclear cells (BMMNC) were prepared by density gradient separation using Lymphoprep™ (Nycomed Pharma, Oslo, Norway) as previously described by Zannettino et al., 1998. Following centrifugation at 400×g for 30 minutes at 4° C., the buffy layer is removed with a transfer pipette and washed three times in "HHF", composed of Hank's balanced salt solution (HBSS; Life Technologies, Gaithersburg, MD), containing 5% fetal calf serum (FCS, CSL Limited, Victoria, Australia).

STRO-3+ (or TNAP+) cells were subsequently isolated by magnetic activated cell sorting as previously described by Gronthos & Simmons, 1995; and Gronthos, 2003. Briefly, approximately 1-3×$10^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mg^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 min. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International publication WO 2006/108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

Example 2 Clinical Study

Clinical Study Design

An objective of this study is to evaluate the safety and feasibility of a single intravitreal injection of 93,750 allogenic MPCs in subjects undergoing Lucentis® therapy.

Another objective is explore functional efficacy of intravitreal MPC on visual acuity, overall mean composite National Eye Institute Visual Function Questionnaire (NEI VFQ-25) and Optical Coherence Tomography (OCT).

Another objective is to reduce the number of anti-VEGF injections needed to prevent leakiness of blood vessels.

Trial design: PhaseIb/IIa randomized, placebo-controlled, study to address the safety and feasibility of a single intravitreal injection of allogeneic MPCs in subjects with newly diagnosed neovascular AMD after ×3 monthly injections of Lucentis® therapy.

Protocol: All patients received ×3 monthly intravitreal Lucentis® injections. In month four, all patients (N=9) to be randomized 2:1 to a single MPC injection or placebo.

Investigational Products and Administration

The investigational product was STRO-3 selected allogeneic MPCs, which were derived from adult bone marrow mononucleated cells that were culture-expanded and subsequently cryopreserved. The allogeneic MPCs were formulated in concentrations of 30-million and 90-million nucleated cells in a 5 mL volume and cryopreserved in 7.5% dimethylsulfoxide/50% alpha modified Eagle's medium and 42.5% ProFreeze®.

The investigational product was stored in the vapor phase of liquid nitrogen at −140° C. to −196° C. until ready for use. The investigational product was to be appropriately identified and segregated from other products.

The doses for this study were 93,750 MPCs (0.03 mL from a 3 million MPC/1 mL bag) and 312,500 MPCs (0.05 mL from a 6 million MPC/1 mL bag). If doses are expressed relative to the vitreous volume of the eye, the starting dose in this study is approximately 24,500 MPCs per mL of vitreous humor.

National Eye Institute Visual Function Questionnaire (NEI VFQ-25)

The NEI VFQ-25 was developed to measure patients' perception of vision-related function see, for example, (Mangione et al., Arch Ophthamol. 116:1496-1505 (1998); and Mangione et al., Arch Ophthamol. 119:1050-1058 (2001).

Figures 2A, 2B, 2C, 2D:
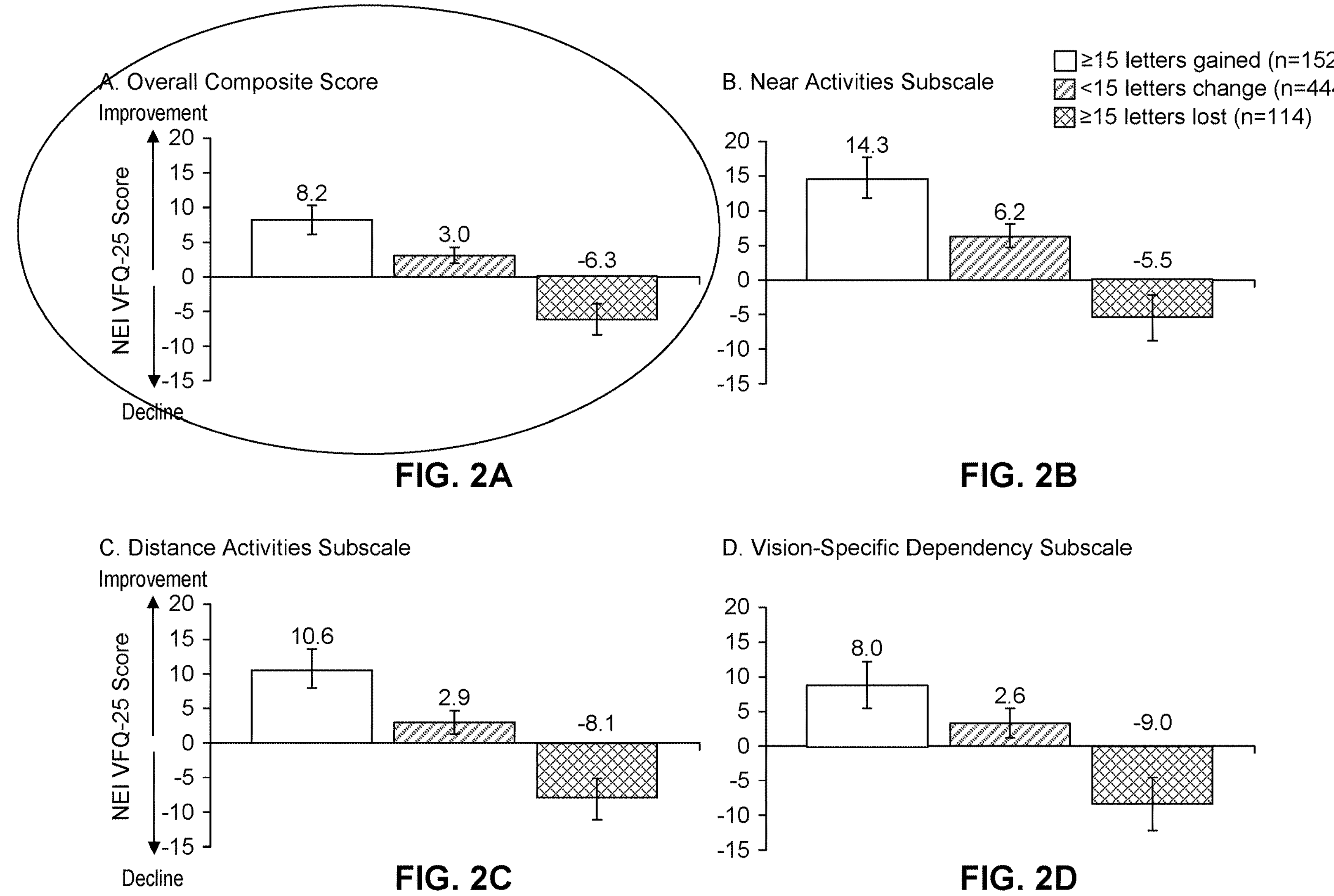
FIGS. 2A-2D are from Responsiveness of NEI VFQ-25 to Changes in Visual Acuity in Neovascular AMD: Validation Studies from Two Phase 3 Clinical Trials" (Invest. Opthalmol. Vis. Sci. 2009; 50(8)3629-3635. doi:10.1167/iovs.08-3225.) MARINA: the least-squares mean change from baseline in NEI VFQ-25 scores for patients who gained ≥15 letters, gained or lost <15 letters, and lost ≥15 letters for the overall composite score (2A) and the three pre-specified subscales: near activities (2B), distance activities (2C), and vision-specific dependency (D2) at 12 months. Error bars represent 95% CI of the mean.

Results published by Suner et al in 2009 (Suner et al., Inv Ophthamol. & Visula science, 50(8): 3629-3635) support the use of the NEI VFQ-25 as a responsive and sensitive measure of vision-related function in neovascular AMD populations. Based on ANCHOR (FIG. 1) and MARINA (FIG. 2) data, a 4- to 6-point change in NEI VFQ-25 scores represents a clinically meaningful change corresponding to a 15-letter change in BCVA.

The NEI VFQ-25 demonstrated responsiveness and sensitivity to clinically meaningful changes in visual acuity in the MARINA and ANCHOR trials. There are marked differences among the three visual acuity subgroups (≥15 letters gained, <15 letters lost or gained, or ≥15 letters lost) in the composite score and the three pre-specified endpoints of near activities, distance activities, and vision-specific dependency. This study provides evidence that the NEI VFQ-25 is responsive to visual acuity changes in patients receiving pharmacologic therapy for neovascular AMD.

Clinical Study Results

Figure 3:
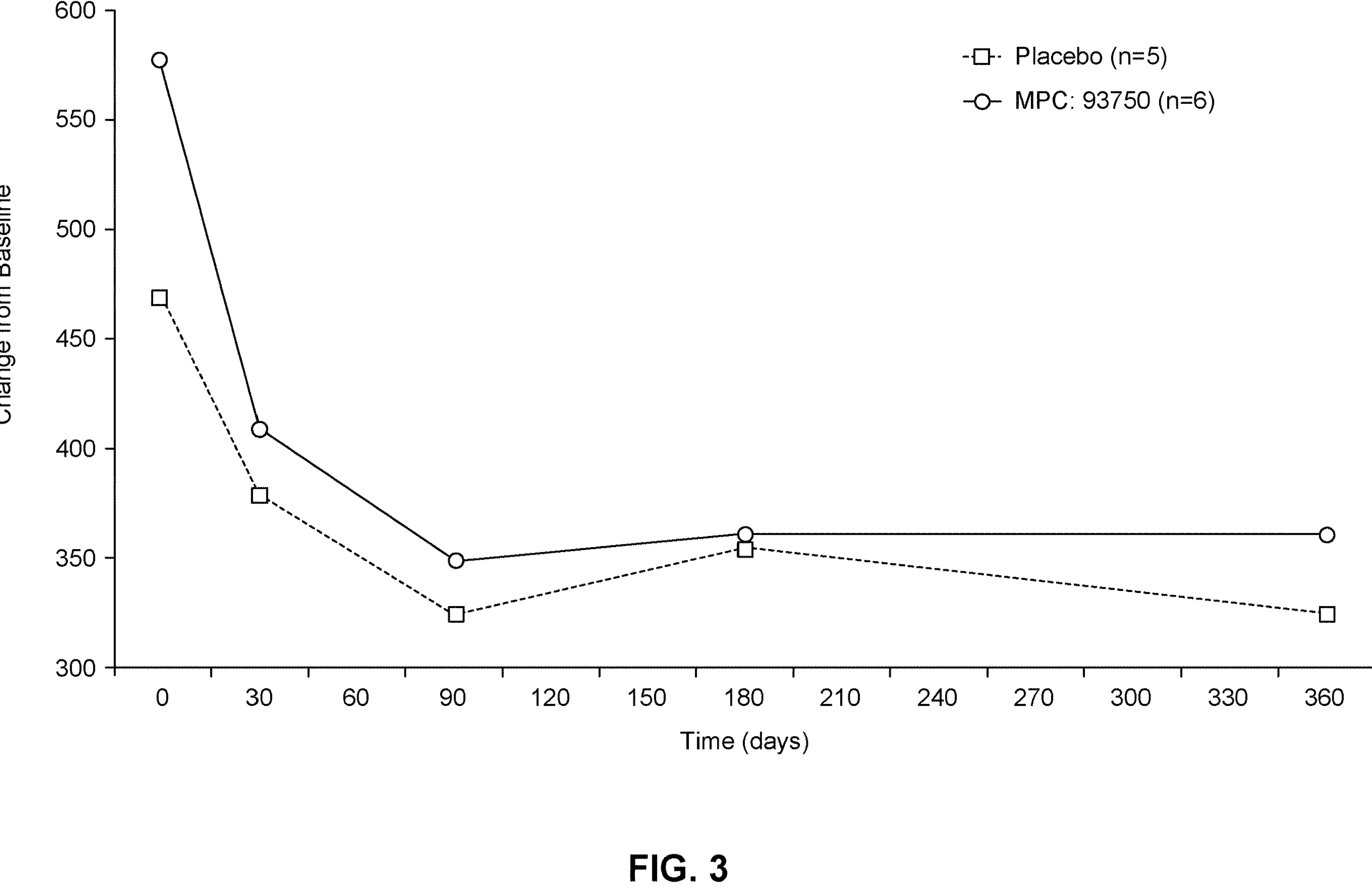
FIG. 3: Change in Neovascular Membrane Thickness as measured by optical coherence tomograph (OCT) following ×3 monthly Lucentis® injections and subsequently either treatment with a single Intravitreal MPC injection or placebo.

FIG. 3 shows change in optical coherence tomography (OCT) in patients who received ×3 monthly Lucentis® injections followed in month 4 by either a single intravitreal MPC injection or placebo. Both patient groups showed a similar and significant reduction in retinal thickness by 3 months, as measured by OCT, consistent with a similar treatment effect of the 3 monthly Lucentis® injections in each group. This indicates that aberrant neovascularization and perivascular extravascular fluid accumulation associated with inflammation were significantly reduced prior to MPC injection. From month 4 onward the degree of change in OCT did not differ between groups, indicating that MPC injection did not further augment aberrant neovascularization and vascular leakiness beyond the initial treatment with Lucentis®.

Figure 4:
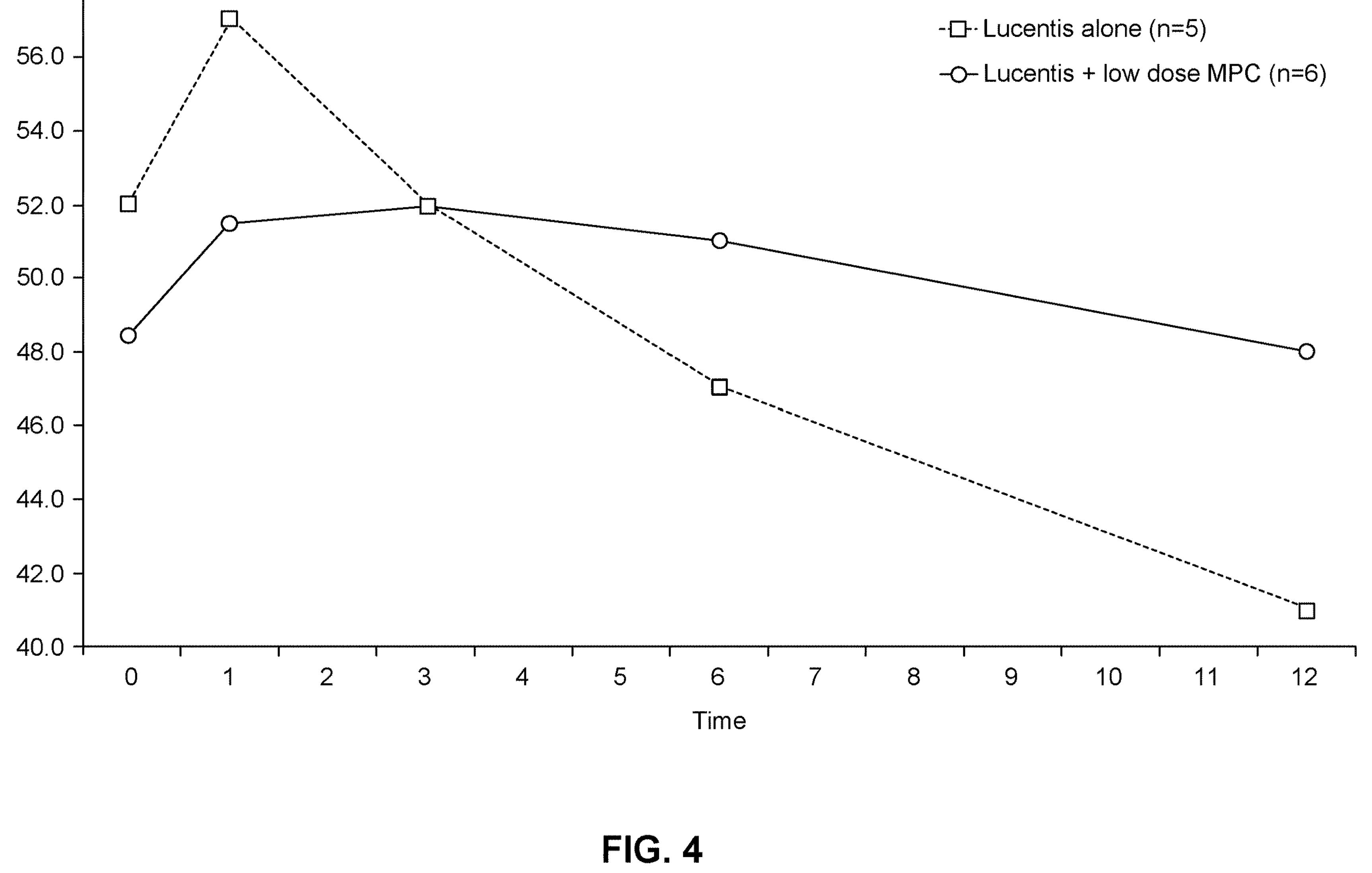
FIG. 4: Efficacy results for visual acuity: median values for patients treated with Lucentis® alone and Lucentis®+ MPCs.

FIG. 4 shows efficacy results in terms of visual acuity score from baseline. The results show median values for patients treated with Lucentis® alone and patients treated with Lucentis® and a single injection of MPCs. Compared with the Lucentis® alone group, who showed significant deterioration in visual acuity over 12 months, those who received a single MPC injection demonstrated maintenance of visual acuity over this time period.

Figure 5:
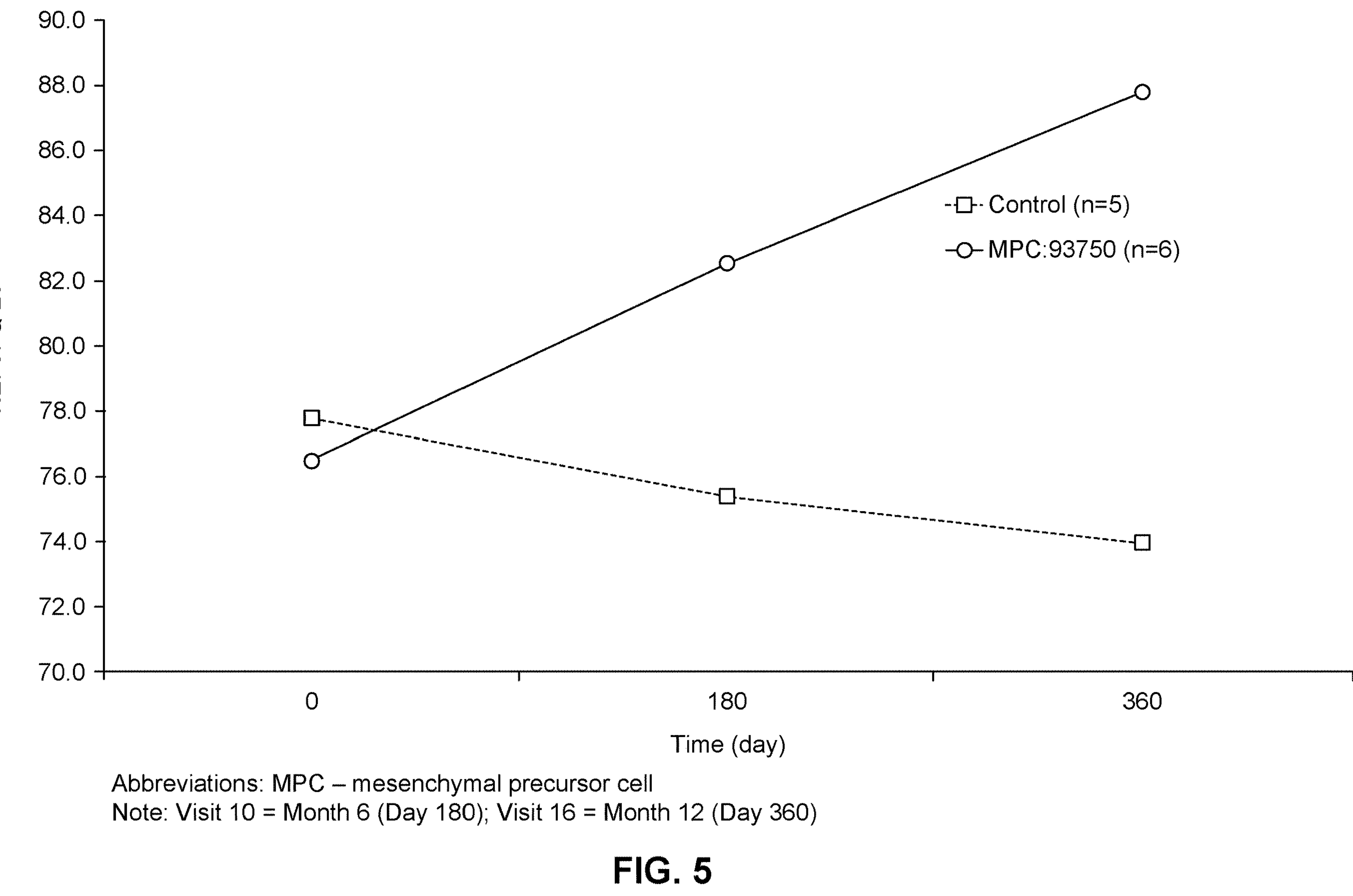
FIG. 5: Single Intravitreal MPC Injection in Lucentis® Treated Patients Results in Significant Improvement in NEI VFQ-25.

FIG. 5 shows NEI VFQ-25 results following a single intravitreal MPC injection in Lucentis® treated patients compared to control Lucentis® treated patients who received a placebo.

These results show that an MPC injection following Lucentis® treatment is effective in:

i. Prevention of loss of visual acuity and stabilisation over 12 months; and ii. 11-point improvement from baseline in composite NEI VFQ-25 score in the MPC+Lucentis® group, compared with a 3-point loss in the Lucentis® group alone, indicating that the MPC group is likely to experience an improvement in visual acuity over 12 months of at least 15 letters while the control group is likely to lose up to the same amount in acuity.

These results indicate that in patients with neovascular AMD in whom Lucentis® has adequately treated the neovascular component and has adequately reversed the inflammatory thickening of the neovascular membrane caused by vascular leakage and perivascular fluid, a single MPC injection is effective in improving visual acuity compared to those Lucentis® treated patients who received a placebo. Since both groups subsequently continued to receive the same number of additional Lucentis® injections as needed, this indicates that the MPCs are improving visual acuity by acting directly on the optic nerve since any neovascularisation or inflammation present in the eye had been adequately treated with the previous monthly injections of Lucentis®.

REFERENCE S

Ausubel, F. M. (Ed.). (1987 including all updates until present). *Current Protocols in Molecular Biology*. New York: John Wiley & Sons.

Brown, T. A. (Ed.). (1991). *Essential Molecular Biology: A Practical Approach* (Vol. 1 and 2). Oxford: IRL Press at Oxford University Press.
Buchschacher & Panganiban (1992). *Journal of Virology,* 2731-2739.
Burns et al., (1993). *Proceedings of the National Academy of Sciences USA,* 8033-8037.
Carter (1992). *Current Opinion in Biotechnology,* 533-539.
Chinnadurai et al., (2016). *Translational and Clinical Research,* 34(9), 2429-2442.
Coligan, J. E., Kruisbeek, A. M., Margulies, D. H., Shevach, E. M., & Strober, W. (Eds.). (1991 including all updates until present). *Current Protocols in Immunology*. New York: John Wiley & Sons.
Fisher-Hoch et al., (1989). *Proceedings of the National Academy of Sciences USA,* 56, 317-321.
Francois et al., (2012). *Cytotherapy,* 14(2), 147-152.
Glover, M., & Hames, B. D. (Eds.). (1995 and 1996). *DNA Cloning: A Practical Approach* (Vols. 1-4).
Gronthos (2003). *Journal of Cell Science,* 116(Pt 9), 1827-1835.
Gronthos & Simmons (1995). *Blood,* 85(4), 929-940.
Harlow, E., & Lane, D. (1988). *Antibodies: A Laboratory Manual*. New York: Cold Spring Harbor Laboratory Press.
Johann et al., (1992). *Journal of Virology,* 65, 1635-1640.
Kotin (1994). *Human Gene Therapy,* 793-801.
Lebkowski et al., (1988). *Molecular and Cellular Biology,* 3988-3996.
Miller (1990). *Human Gene Therapy,* 7, 5-14.
Miller & Rosman (1989). *Biotechniques,* 7, 980-990.
Miller et al., (1991). *Journal of Virology,* 65, 2220-2224.
Muzyczka (1992). *Current Topics in Microbiology and Immunology,* 158, 97-129.
Perbal, B. V. (1984). *A Practical Guide to Molecular Cloning*. New York: Wiley.
Sambrook, J., & Green, M. R. (2012). *Molecular Cloning: A Laboratory Manual* (*Fourth Edition*). New York: Cold Spring Harbour Laboratory Press.
Scarpa et al., (1991). *Virology,* 75, 849-852.
Sommerfelt & Weiss (1990). *Virology,* 76, 58-59.
Vincent et al., (1990). *Vaccine,* 353-359.
Wilson et al., (1989). *Journal of Virology,* 63, 2374-2378.
Zannettino et al., (1998). *Blood,* 92(8), 2613-26

The invention claimed is:

1. A method of improving visual acuity in a human subject suffering from an ocular disease, the method comprising administering to the subject a composition comprising mesenchymal lineage precursor or stem cells (MLPSCs) in an amount sufficient to improve visual acuity as measured by the National Eye Institute Visual Function Questionnaire-25 (NEI VFQ-25), wherein the ocular disease comprises degradation or inflammation of the optic nerve, and wherein treatment with an anti-VEGF agent has reduced neovascularisation in the optic tissue of the subject prior to the administration of the MLPSCs.

2. The method of claim 1, wherein the subject has been treated with a monthly dosage of the anti-VEGF agent for least 3 months prior to the administration of the MLPSCs.

3. The method of claim 1, wherein the anti-VEGF agent is an anti-VEGF antibody or fragment thereof.

4. The method of claim 1, wherein the mesenchymal lineage precursor or stem cells were isolated by immunoselection prior to the administration.

5. The method of claim 4, wherein the immunoselected cells were culture expanded prior to the administration.

6. The method of claim 1, wherein the mesenchymal lineage precursor or stem cells are culture expanded mesenchymal stem cells.

7. The method of claim 1, wherein the MLPSCs are administered to the subject at a dose of less than 350,000 cells, or less than 250,000 cells, or less than 100,000 cells, or less than 95,000 cells, or less than 90,000 cells or less than 80,000 cells, or less than 75,000 cells, or less than 70,000 cells.

8. The method of claim 1, wherein the MLPSCs are administered to the subject at a dose of less than 100,000 cells per mL of vitreous humor, or less than 75,000 cells per mL of vitreous humor, or less than 50,000 cells per mL of vitreous humor, or less than 25,000 cells per mL of vitreous humor, less than 20,000 cells per mL of vitreous humor.

9. The method of claim 1, wherein the MLPSCs are administered to the subject at a dose of about 24,500 mesenchymal precursor cells (MPCs) per mL of vitreous humor.

10. The method of claim 1, wherein the MLPSCs are administered as a single dose.

11. The method of claim 1, wherein the MLPSCs are administered intravitreally.

12. The method of claim 1, wherein the administration of the MLPSCs results in at least a 10-point improvement from baseline in composite NEI VFQ-25 score within at least a 6 month period.

13. The method of claim 1, wherein the administration of the MLPSCs results in at least a 10-point improvement from baseline in composite NEI VFQ-25 score that is maintained for at least a 3 month period.

14. The method of claim 1, wherein the ocular disease is neovascular AMD.

15. The method of claim 2, wherein the MLPSCs are administered at least one month after the 3 monthly doses of the anti-VEGF agent.

* * * * *